US00RE46584E

(19) United States
(12) Reissued Patent
Dresios et al.

(10) Patent Number: US RE46,584 E
(45) Date of Reissued Patent: Oct. 24, 2017

(54) METHODS AND COMPOSITIONS FOR WOUND TREATMENT

(71) Applicant: Leidos, Inc., Reston, VA (US)

(72) Inventors: John Dresios, Carlsbad, CA (US); Richard Holmes Griffey, Vista, CA (US)

(73) Assignee: Leidos, Inc., Reston, VA (US)

(21) Appl. No.: 15/006,882

(22) Filed: Jan. 26, 2016

Related U.S. Patent Documents

Reissue of:
(64) Patent No.: 8,663,932
Issued: Mar. 4, 2014
Appl. No.: 13/332,738
Filed: Dec. 21, 2011

U.S. Applications:
(60) Provisional application No. 61/425,491, filed on Dec. 21, 2010, provisional application No. 61/426,882, filed on Dec. 23, 2010.

(51) Int. Cl.

| | |
|---|---|
| ***G01N 33/53*** | (2006.01) |
| ***C07K 16/00*** | (2006.01) |
| ***A61K 47/42*** | (2017.01) |
| ***G01N 33/567*** | (2006.01) |
| ***A61K 39/44*** | (2006.01) |
| ***C07K 16/18*** | (2006.01) |
| ***A61K 9/127*** | (2006.01) |
| ***A61K 38/02*** | (2006.01) |
| ***G01N 33/50*** | (2006.01) |
| *A61K 47/48* | (2006.01) |
| *A61K 38/17* | (2006.01) |

(52) U.S. Cl.
CPC ..... *A61K 47/42* (2013.01); *A61K 9/1271* (2013.01); *A61K 38/02* (2013.01); *A61K 39/44* (2013.01); *C07K 16/18* (2013.01); *G01N 33/5088* (2013.01); *G01N 33/567* (2013.01); *A61K 38/1777* (2013.01); *A61K 47/48376* (2013.01); *A61K 47/48384* (2013.01); *A61K 47/48415* (2013.01); *A61K 47/48553* (2013.01)

(58) Field of Classification Search
CPC ..... A61K 47/42
See application file for complete search history.

(56) References Cited

U.S. PATENT DOCUMENTS

| | | | | |
|---|---|---|---|---|
| 4,957,735 | A | 9/1990 | Huang | 424/85.8 |
| 5,780,052 | A | 7/1998 | Khaw et al. | 424/450 |
| 5,955,343 | A | 9/1999 | Holmes et al. | 435/240.1 |
| 7,347,998 | B2 | 3/2008 | Hall et al. | 424/93.2 |
| 7,527,936 | B2 | 5/2009 | Xu et al. | 435/7.21 |
| 7,780,882 | B2 | 8/2010 | Chang et al. | 264/4.1 |
| 7,820,157 | B2 | 10/2010 | Hall et al. | 424/93.2 |
| 2002/0103112 | A1* | 8/2002 | Ferguson et al. | 514/2 |
| 2007/0065415 | A1 | 3/2007 | Kleinsek et al. | 424/93.7 |
| 2008/0241233 | A1 | 10/2008 | Sims et al. | 424/450 |
| 2009/0036349 | A1 | 2/2009 | Ruoslahti et al. | 514/2 |
| 2009/0263468 | A1 | 10/2009 | McAnulty et al. | 424/443 |
| 2010/0008973 | A1 | 1/2010 | Galili | 424/443 |
| 2010/0129430 | A1 | 5/2010 | Sofou | 424/450 |
| 2011/0038920 | A1* | 2/2011 | Mori et al. | 424/445 |

OTHER PUBLICATIONS

Wright, N. T. and Humphrey, J. D., "Denaturation of Collagen Via Heating: An Irreversible Rate Process," *Annu. Rev. Biomed. Eng.* 4, 109-128, 2002.

Davis, G. E., "Affinity of Integrins for Damaged Extracellular Matrix: $a_v\beta_3$ Binds to Denatured Collagen Type I Through RGD Sites," Biochem. Biophys. Res. Commun, vol. 182, No. 3, 1025-1031, 1992.

Pfaff, M., et al., "Integrin and Arg-Gly-Asp Dependence of Cell Adhesion to the Native and Unfolded Triple Helix of Collagen Type VI," *Exp. Cell Res.* 206, 167-176, 1993.

Mogford, J. E., Davis, G. E., Platts, S.H., Meininger, G. A., "Vascular Smooth Muscle $a_v\beta_3$ Integrin Mediates Arteriolar Vasodilation in Response to RGD Peptides," Circ. Res. 79(4):821-826, 1996.

D'Souza, S . E . , et al., "Ligand and Cation Binding are Dual Functions of a Discrete Segment of the Integrin $\beta_3$ Subunit: Cation Displacement is Involved in Ligand Bindings," Cell, vol. 79, 659-667, Nov. 18, 1994.

Yokoi et al., "Dynamic Reassembly of Peptide RADA16 nanofiber Scaffold," *Proc. Natl. Acad. Sci. USA,* vol. 102, No. 24, 8414-8419, Jun. 14, 2005.

Ellis-Behnke, R. G., et al., "Nano Hemostat Solution: Immediate Hemostasis at the Nanoscale," Nanomedicine: Nanotechnology, Biology, and Medicine, 2, 207-215, 2006.

Amin Hajitou, Renata Pasqualini, and Wadih Arap, "Vascular Targeting: Recent Advances and Therapeutic Perspectives," TCM, vol. 16, No. 3, 2006.

Martin Trepel, Renata Pasqualini, and Wadih Arap, "Screening Phage-Display Peptide Libraries for Vasular Targeted Peptides," Chapter 4, Methods in Enzymology, vol. 445, Elsevier, Inc., Copyright 2008.

Agnihotri, S.A., Mallikarjuna, N.N., Aminabhavi, T.M., "Recent Advances on Chitosan-Based Micro- and Nanoparticles in Drug Delivery," J. Control Release, 100, 5-28, 2004.

Balthasar, S., Michaelis, K., Dinauer, N., von Briesen, H., Kreuter, J., Langer, K., "Preparation and Characterisation of Antibody Modified Gelatin Nanoparticles as Drug Carrier System for Uptake in Lymphocytes," Biomaterials, 26, 2723-2732, 2005.

Challa, R., Ahuja, A., Ali, J., Khar, R.K., "Cyclodextrins in Drug Delivery: An Updated Review," AAPS PharmSciTech, 6(2), Article 43, E329-E357, 2005.

(Continued)

*Primary Examiner* — Johnny F Railey
(74) *Attorney, Agent, or Firm* — Dawn-Marie Bey; Bey & Cotropia PLLC

(57) ABSTRACT

The present disclosure relates to methods for identifying proteins or peptide motifs of intracellular, extracellular, or extracellular matrix proteins specifically exposed in wound sites, as well as compositions for treating wounds, and methods for their use.

8 Claims, 12 Drawing Sheets

(56) References Cited

OTHER PUBLICATIONS

Emoto, K., Nagasaki, Y., Iijima, M., Kato, M., Kataoka, K., "Preparation of Non-Fouling Surface Through the Coating With Core-Polymerized Block Copolymer Micelles Having Aldehyde-Ended PEG Shell," Colloids and Surfaces B: Biointerfaces, 18, 337-346, 2000.
Gasper, M.M., Blanco, D., Cruz, M.E., Alonso, M.J., "Formulation of L-asparaginase-loaded poly(lactide-co-glycolide) nanoparticles: influence of polymer properties on enzyme loading, activity and in vitro release," J. Control Release, 52, 53-62, 1998.
Gref, R., Couvreur, P., Barratt, G., Mysiakine, E., "Surface-Engineered Nanoparticles for Multiple Ligand Coupling," Biomaterials, 24, 4529-4537, 2003.
Gref, R., Minamitake, Y., Peracchia, M.T., Trubetskoy, V., Torchilin, V., Langer, R., "Biodegradable Long-Circulating Polymeric Nanospheres," Science, vol. 263, 1600-1603, Mar. 18, 1994.
Huwyler, J., Wu, D., Pardridge, W.M., "Brain Drug Delivery of Small Molecules Using Immunoliposomes," Proc. Natl. Acad. Sci. USA, vol. 93, 14164-14169, Nov. 1996.
Kang, Y.S., Saito, Y., Pardridge, W.M., "Pharmacokinetics of [$^3$H]Biotin Bound to Different Avidin Analogues," J. Drug Targeting, vol. 3, 159-165, 1995.
Landry, F.B., Bazile, D.V, Spenlehauer, G., Veillard, M., Kreuter, J., "Degradation of poly(D,L-lactic acid) nanoparticles coated with albumin in model digestive fluids (USP XXII)," Biomaterials, 17, 715-723, 1996.
Li, J.K., Wang, N., Wu, X.S., "A Novel Biodegradable System Based on Gelatin Nanoparticles and Poly(lactic-co-glycolic acid) Microspheres for Protein and Peptide Drug Delivery," J. Pharm Sci., vol. 86, No. 8, 891-895, Aug. 1997.
Lukyanov, A,N., Torchilin, V.P., "Micelles From Lipid Derivatives of Water-Soluble Polymers as Delivery Systems for Poorly Soluble Drugs," Adv. Drug Deliv. Rev. 56, 1273-1289, 2004.
Olivier, J.C., "Drug Transport to Brain With Targeted Nanoparticles," NeuroRx., vol. 2, 108-119, 2005.
Olivier, J.C., Huertas, R., Lee, H.J., Calon, F., Pardridge, W.M., "Synthesis of Pegylated Immunonanoparticles," Pharm. Res., vol. 19, No. 8, 1137-1143, Aug. 2002.
Praetorius, N. P. and Mandal, T. K., "Engineered Nanoparticles in Cancer Therapy," Recent Patents on Drug Delivery & Formulation, 1, 37-51, 2007.
Rijcken, C.J., Soga, O., Hennink, W.E, van Nostrum, C.F., "Triggered Destabilisation of Polymeric Micelles and Vesicles by Changing Polymers Polarity: An Attractive Tool for Drug Delivery," J. Control Release, 120, 131-148, 2007.
Salem, A.K., et al., "Synthesis and Characterisation of a Degradable Poly(lactic acid)-Poly(ethylene glycol) Copolymer With Biotinylated End Groups," Biomacromolecules, 2, 575-580, 2001.
Soppimath, K.S., Aminabhavi, T.M., Kulkarni, A.R., Rudzinski, W.E., "Biodegradable Polymeric Nanoparticles as Drug Delivery Devices," J. Control Release, 70, 1-20, 2001.
Tessmar, J., Mikos, A., Gopferich, A., "Amine-Reactive Biodegradable Diblock Copolymers," Biomacromolecules, 3, 194-200, 2002.
Tessmar, J., Mikos, A., Gopferich, A., "The Use of Poly(ethylene glycol)-block-Poly(lactic acid) Derived Copolymers for the Rapid Creation of Biomimetic Surfaces,{" Biomaterials, 24, 4475-4486, 2003.
Torchilin, V.P., "Drug Targeting," Eur. J. Pharm. Sci. 11, Suppl 2, S81-S91, 2000.
Wang, N., Wu, X.S., Li, J.K., "A Heterogeneously Structured Composite Based on Poly(lactic-co-glycolic acid) Microspheres and Poly(vinyl alcohol) Hydrogel Nanoparticles for Long-Term Protein Drug Delivery,". Pharm. Res., vol. 16, No. 9, 1430-1435, 1999.
Yamamoto, Y., Nagasaki, Y., Kato, M., Kataoka, K., "Surface Charge Modulation of Poly(ethylene glycol)-poly(D,L-lactide) Block Copolymer Micelles: Conjugation of Charged Peptides," Colloids and Surfaces B: Biointerfaces, 16, 135-146, 1999.
Yamamoto, Y., Nagasaki, Y., Kato, Y., Sugiyama, Y., Kataoka, K., "Long-Circulating Poly(ethylene glycol)-Poly(D,L-lactide) Block Copolymer Micelles With Modulated Surface Charge," J. Control Release, 77, 27-38, 2001.
Yang, H., Lopina, S.T., "In Vitro Enzymatic Stability of Dendritic Peptides," J. Biomed. Mater. Res. 76, 398-407, 2006.
International Search Report and Written Opinion for Application No. PCT/US11/66353, dated Apr. 9, 2012, 9 pp.
Skalli, et al., "Monocional Antibody Against a-Smooth Muscle Actin: A New Probe for Smooth Muscle Differentiation," The Journal of Cell Biology, vol. 103, pp. 2787-2796, 1986.
Mellgren, Ronald, "A Plasma Membrane Wound Proteome: Reversible Externalization of Intracellular Proteins Following Reparable Mechanical Damage," JBC, vol. 285, No. 47, pp. 36597-36607, Nov. 2010.
Supplementary European Search Report for Application No. EP 11 85 2145, dated Jun. 18, 2015, 7 pp.
J. A. Andrades, et al., "Engineering, Expression, and Renaturation of a Collagen-Targeted Human bFGF Fusion Protein," Growth Factors Journal, vol. 18, pp. 261-275, 2001.
Wenxue Zhao, et al., "Vascularization and Cellularization of Collagen Scaffolds Incorporated With Two Different Collagen-Targeting Human Basic Fibroblast Growth Factors," Journal of Biomedical Materials Research, Part A, DOI 10.1002/jbm.a, Wily Periodicals, Inc., pp. 630-636, 2007.
Majesky et al. PDGF ligand and receptor gene expression during repair of arterial injury. The Journal of Cell Biology 1990, vol. 111, pp. 2149-2158.*
Mejean et al. Anti-actin antibodies. An immunological approach to the myosin-actin and the tropomyosin-acitn interfaces. Biochem. J. 1987, vol. 244, pp. 571-577.*
Jockusch et al. An effecient method of produce specific anti-actin. Histochemistry 1978, vol. 55, pp. 177-184.*
Vaiyapuri, Sakthivel, Ph.D., et al., "Gap Junctions and Connexin Hemichannels Underpin Haemostasis and Thrombosis," Europe PMC Funders Group, Author Manuscript, Available in PMC Nov. 22, 2012 (Circulation, May 22, 2012; 125(20); 2479-2491, doi: 10.1161/CIRCULATIONAHA.112.101246).
Shinohara, Mari L., et al. "Alternative translation of Osteopontin Generates Intracellular and Secreted Isoforms that Mediate Distinct Biological Activities in Dendritic Cells," PNAS, vol. 105, No. 20, pp. 7235-7239, May 20, 2008.
Andrea, Johanna, et al. "Role of Platelet-Derived Growth Factors in Physiology and Medicine" [online], Copyright 2008 retrieved on Sep. 3, 2013, Genes & Development, 22:1276-1312, by Cold Spring Harbor Laboratory Press, ISSN 0890-9369/08, Retrieved from the Internet: genesdev.cshlp.org.

* cited by examiner

Exposure of a Protein Target in Wounded Tissue

Specific Exposure of a Protein Target in Wounded Tissue

Specific Exposure of a Protein Target in Wounded Tissue

Specific Exposure of an Extracellular Protein Domain Target (RGD tripeptide) in Wounded Rat Liver Tissue Specific Exposure of Actin Protein in Wounded Rat Spleen Targeting of an Wound-Specific Epitope in the Presence of Blood Kinetic Evaluation of Wound-Specific Targeting Wound-Specific Exposure of Actin Epitopes in Swine Liver Beads Conjugated to Anti-Actin Recognize Wounded Liver Tissue (A) (B)

Validation of Wound-Specific Markers *In Vivo*

Assessment of wound specific exposure of ribosomal protein S6

Reduction in Blood Loss upon Treatment with a Self-Assembling Peptide

Liposomes Carry Protein Payload to Wounded Tissue

METHODS AND COMPOSITIONS FOR WOUND TREATMENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application claims priority, pursuant to 35 U.S.C. §119(e), to the filing date of U.S. Provisional Patent Application Ser. Nos. 61/425,491 and 61/426,882 filed 21 Dec. 2010 and 23 Dec. 2010, the disclosures of which are herein incorporated by reference in their entirety.

STATEMENT REGARDING GOVERNMENT INTEREST

This invention was made with Government support under Contract Number W911NF-10-C-0065 awarded by the Defense Advanced Research Projects Agency. The Government has certain rights in this invention.

INTRODUCTION

The present disclosure relates to methods for identifying proteins and peptide motifs exposed in wound sites, compositions for treating wounds, and methods for their use.

BACKGROUND

Conventional treatment of wounds includes the use of tourniquets, local application of hemostatic agents (powders, sutures, staples, adhesives, tapes) that require mechanical compression, and, in certain cases, cauterization of the wound itself. These techniques function in part to seal the wound from exposure to infection, prevent blood loss, and to initiate the body's natural wound healing process. However, these techniques are ineffective for direct treatment of intracavitary, non-compressible wounds, such as, for example, from a bomb shock wave where internal injuries can occur without visible external injury. A need exists for active agents and associated delivery systems that could be used by a layperson, such as a soldier, to rapidly stop bleeding in the field, and/or treat non-compressible wounds, such as trunk wounds which cause the majority of battlefield deaths. A need also exists for methods and compositions for treatment of a subject having internal wounds, particularly in non-compressible areas such as internal organs damaged by a shock wave. A need also exists for methods and compositions to assist in attenuating blood loss and/or to support and promote the healing process in wounds resulting from burns or penetration by a foreign object or surgical incision, particularly prior to or at the time of wound closure.

SUMMARY

In some aspects, the present disclosure provides a method for identifying a wound target, wherein the wound target is an exposed protein, peptide motif or epitope, wherein the exposed protein, peptide motif or epitope becomes exposed upon wounding, the method comprising: a) wounding a tissue; b) incubating the tissue with a detectable wound targeting moiety; c) washing away unbound wound targeting moiety; d) detecting whether the wound targeting moiety is specifically bound to an exposed protein, peptide motif or epitope; and e) identifying the exposed protein, peptide motif or epitope specifically bound upon wounding as a wound target. In some embodiments, the tissue is ex vivo. In some embodiments, the tissue is in vivo in a subject.

In some aspects, provided is a method for treatment of an open wound in a subject, comprising administering to the open wound a composition comprising a carrier, an active agent, and a wound targeting moiety, wherein the wound targeting moiety facilitates local delivery of the active agent to wounded tissue by binding to an exposed protein, peptide motif or epitope, wherein the exposed protein, peptide motif or epitope is exposed upon wounding of the subject. In some embodiments, the protein or peptide motif resides in a tissue selected from the group consisting of epithelial tissue, connective tissue, muscle tissue, and nerve tissue. In some embodiments, the connective tissue is selected from the group consisting of bone, cartilage, tendon, and ligaments.

In some aspects, provided is a composition for administration to an open wound in a subject, comprising a carrier, an active agent and a wound targeting moiety, wherein the wound targeting moiety facilitates local delivery of the active agent to wounded tissue by selectively binding to an exposed protein, peptide motif or epitope, wherein the exposed protein, peptide motif or epitope is exposed upon wounding of the subject.

In some aspects, provided is a method for treatment of an internal wound in a subject, comprising administering to the subject a composition comprising a carrier containing an active agent and displaying a wound targeting moiety, wherein the wound targeting moiety facilitates local delivery of the active agent to injured tissue by binding to an intracellular protein or a peptide motif of an intracellular, extracellular, or extracellular matrix protein that is exposed by displacement from its natural location. In some embodiments, the protein or peptide motif, or epitope thereof, is exposed by cell lysis or rupture. In some embodiments, the protein or peptide motif, or epitope thereof, is exposed upon denaturation of an extracellular matrix protein.

In some aspects, provided is a composition for treatment of an internal wound in a subject, comprising a carrier, an active agent and a wound targeting moiety, wherein the wound targeting moiety facilitates local delivery of the active agent to wounded tissue by selectively binding to an exposed protein, peptide motif or epitope, wherein the exposed protein, peptide motif or epitope is exposed upon wounding of the subject. In some embodiments, the protein, peptide motif or epitope is exposed by displacement from its natural location.

The methods of treatment and compositions for treatment disclosed herein are advantageous in minimizing the amount of therapeutic agents that must be delivered to a site and in improving the specificity of delivery to the critical site of tissue damage. The methods and compositions further allow access to non-compressible, asymmetrically exposed and intracavitary areas, irrespective of geometry and location.

DETAILED DESCRIPTION

Figure 1:
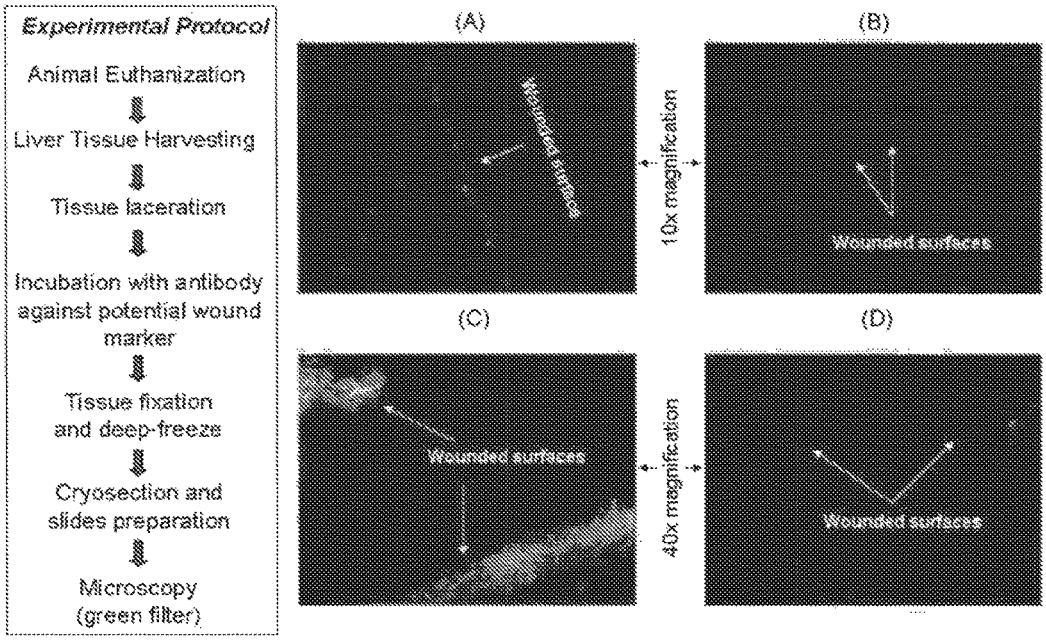
FIG. 1 illustrates exposure of a protein target (actin) in wounded rat liver tissue.

Several embodiments of the present disclosure are described in detail hereinafter. These embodiments may take many different forms and should not be construed as limited to those embodiments explicitly set forth herein. Rather, these embodiments are provided so that this disclosure will be thorough and complete, and will fully convey the scope of the present disclosure to those skilled in the art.

Definitions

As used herein, the singular forms "a," "an," and "the" include plural referents unless the context clearly dictates otherwise. Thus, for example, reference to a "monocot plant" can mean, for example, a single monocot plant, such as a rice plant, or it can mean two or more of the same or different species of monocot plants.

As used herein, the term "sequence identity" means nucleic acid or amino acid sequence identity in two or more aligned sequences, aligned using a sequence alignment program.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at (ncbi.nlm.gov/BLAST/). See, also, Altschul, S. F. et al., 1990 and Altschul, S. F. et al., 1997.

The term "% homology" is used interchangeably herein with the term "% identity" and refers to the level of nucleic acid or amino acid sequence identity between two or more aligned sequences, when aligned using a sequence alignment program. For example, 70% homology means the same thing as 70% sequence identity determined by a defined algorithm, and accordingly a homologue of a given sequence has greater than 70% sequence identity over a length of the given sequence. Exemplary levels of sequence identity include, but are not limited to 70%, 75% 80%, 85%, 90% or 95% or more sequence identity to a given sequence, e.g., the coding sequence for transferrin, as described herein.

Sequence searches are typically carried out using the BLASTN program when evaluating a given nucleic acid sequence relative to nucleic acid sequences in the GenBank DNA Sequences and other public databases. The BLASTX program is suitable for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See ncbi.nlm.gov/BLAST/. See, also, Altschul, S. F. et al., 1990 and Altschul, S. F. et al., 1997).

One suitable alignment of selected sequences in order to determine "% identity" between two or more sequences, is performed using, for example, the CLUSTAL-W program in MacVector version 6.5, operated with default parameters, including an open gap penalty of 10.0, an extended gap penalty of 0.1, and a BLOSUM 30 similarity matrix, or similar tools or programs known to those skilled in the art.

Method for Identification of Exposed Intracellular Proteins

In some embodiments of the disclosed method for identifying a wound target, a wound target is an exposed protein, peptide motif or epitope, which becomes exposed at the time of wounding. In some embodiments of this method, a tissue is first lacerated or wounded, then incubated with a detectable wound targeting moiety. The laceration or wound is then washed, which removes unbound wound targeting moiety and allows the detection of the bound wound targeting moiety. If the wound targeting moiety is observed to be specifically bound to an exposed protein, peptide motif or epitope in wounded tissue and does not bind appreciably above background levels to unwounded tissue, the exposed protein, peptide motif or epitope is identified as a wound target. Skilled artisans will understand that there is often non-specific background binding by some targeting agents, and thus, comparison can be made to a negative control, and quantitation may be zeroed or normalized to background levels. In some embodiments, the tissue is ex vivo. In some embodiments, the tissue is in vivo in a subject.

In some embodiments, once a wound target is identified, the amino acid sequence of the protein, peptide motif or epitope is identified, and other proteins, peptide motifs or epitopes having common localization, functional characteristics, or having amino acid sequence similarity to the wound target can considered candidates as possible wound targets. For example, when actin was found as a wound target, other intracellular cytoskeletal proteins with similar intracellular localization and functional characteristics, such as myosin or tubulin, are then considered as candidate wound targets, for testing in the method disclosed herein. Other abundant and/or partially insoluble proteins may also be considered candidate wound targets for testing in the method disclosed herein. As another example, when a cryptic tripeptide arginine-glycine-aspartic acid (RGD) epitope not normally exposed in the native collagen is found to be exposed in response to wounding, other RGD domain-containing proteins are considered candidate wound targets, for testing in the method disclosed herein. Similarly, BLASTX searches for proteins, peptide motifs or epitopes having, for example, 70%, 75% 80%, 85%, 90% or 95% or more amino acid sequence identity over the entire length of the protein, or a peptide motif or epitope, of a wound target (e.g., actin or an RGD-domain-containing protein, as identified herein), can be considered candidate wound targets.

As such, the identification method as disclosed herein allows for identification and confirmation of whether an protein previously unexposed in an uninjured organ or tissue is a suitable target for selective targeting with a therapeutic agent in accordance with the treatment compositions and methods disclosed herein.

The term "intracellular protein" as used in the context of the present identification method refers to any protein(s) normally contained within a cell in an in vivo, unwounded setting, but which may become exposed to an internal or external environment (or extracellular environment) in an injured cell or tissue, or in a wounded subject.

In one embodiment, the identification method utilizes organ and vessel sample tissues. The term "organs" as used herein includes skin, internal organs, and their associated tissues. In some aspects, the tissue is an organ selected from the group consisting of esophagus, stomach, small and large intestines, pancreas, liver, kidney, bladder, urethra, heart, lung, brain, and reproductive organs. The term "vessel" as used herein includes artery, vein, capillary or lymphatic vascular tissues.

Euthanized organisms/animals are employed, and wounding or laceration to the organ or tissue of interest can occur before or after excision from the body. In the case of animal use, suitable tissue samples may be derived from healthy, untreated, pathogen-free, euthanized animals.

As used herein, the term "wounding" means inducing an injury in a tissue, in vivo or ex vivo. A wound can be any tissue-damaging or tissue-penetrating injury, and can include slicing, cutting, puncturing, crushing, and/or shock-wave damage to tissue. A wound can be internal or exposed to the environment, and can include percussive injury. An injury may or may not lyse, rupture or crush cells within the tissue. The term "laceration" as used herein generally refers to injury to the organ or tissue without limit to the depth or shape of the wound, so long as the injury is sufficient to expose an otherwise inaccessible intracellular protein or peptide motif of interest.

After injury, the tissue is treated with a wound targeting moiety, such as an antibody against a known epitope. In some embodiments, the epitope is part of an intracellular protein. In some embodiments, the epitope is part of an extracellular protein. In some embodiments, the epitope is part of an extracellular matrix protein. In one embodiment, the wound target is not an extracellular protein or extracellular matrix protein or peptide motif thereof. In some embodiments, the antibody is an antibody to actin protein or to a ribosomal protein. In some embodiments, the labeled antibody is a fluorescently labeled antibody. Suitable labeled antibodies include those labeled with fluroescein.

In some embodiment, the term "exposed" refers to accessibility of an intracellular or extracellular protein or peptide motif or epitope, wherein the accessibility happens specifically upon wounding. Thus, a highly selective agent, specific for wounded tissue, can be used to bind to the exposed protein, peptide motif or epitope (also known herein as a "exposed wound target" or simply "wound target"). In some embodiments, the wound target makes direct contact with the external environment through the opening in the wound caused by penetrating, surgical, or other trauma. The term "external environment" as used herein refers to the environment that exists outside of the organism suffering from the wound. In some embodiments, the term "exposed" also refers to exposure to an internal environment of the organism, where the term "internal environment" refers to the environment that exists inside of the organism suffering from an internal wound such as a bomb blast where an external open wound may not be present. The internal environment to which an intracellular protein or peptide motif of an intracellular, extracellular, or extracellular matrix protein is exposed to includes blood vessels (arteries and veins) and tissue surrounding the wounded area.

Wound targets can also be identified by screening phage display peptide libraries. For example, see Trepel, et al., (2008) Methods in Enzymology, (445): 83-106).

Multiple antibodies against a protein can be tested with each antibody targeting a different epitope within the protein sequence. Appropriate labeling of these antibodies can be evaluated using standard chromatographic techniques. Tissue samples are lacerated under controlled conditions. In one aspect, undamaged tissue (control) and injured tissue are incubated with labeled (e.g. with fluorescein) primary antibodies against the candidate target epitopes as well as with labeled non-specific antibodies, e.g. IgG or IgM, as negative controls. Tissue samples are then fixed, subjected to fast freezing and cryosectioning using a microtome. Slides containing tissue samples are examined using fluorescence imaging microscopy. Microscopy images are captured and analyzed to assess whether the target epitopes are exposed in wounded but not in healthy tissue areas as a means of their interaction with their cognate labeled antibodies. Examples of this procedure are further described in the Examples section below and in the Figures, where actin is identified as an exemplary target for treatment in an open wound by the compositions and methods disclosed herein.

Carriers

Types of carriers for use in the methods and compositions described herein include but are not limited to soluble polymers, microcapsules, microparticles, cells, cell ghosts, liposomes, micelles, organic or inorganic nanoparticles, self-assembling nanofibers, and dendritic peptides, dendritic organic molecules, or dendritic mixtures of organic molecules. The term "carrier" and "carriers" as used herein are not intended to encompass viral vectors.

Representative examples of carriers include:

Liposomes, i.e. artificially prepared vesicles made of lipid bilayer, including MLV (multilamellar vesicles), SUV (Small Unilamellar Vesicles) and LUV (Large Unilamellar Vesicles);

Nanoparticles composed of natural (e.g. fibronectin, various polysaccharides, albumin, collagen and gelatin) or synthetic (e.g. polyacrylates, polyamides, polysterenes, cyanoacrylates) polymer materials (Soppimath et al., (2001), J. Control Release, 70, 1-20);

Microspheres, including gelatin nanoparticle-poly(lactic-co-glycolic acid) (PLGA) particles (Li et al., (1997) J Pharm Sci. 86, 891-895) as well as nanospheres developed from amphiphilic copolymers composed of biocompatible blocks (Gref et al., (1994) Science, 263, 1600-1603);

Poly(lactide-co-glycolide) (PLG) nanoparticles (Gasper et al., (1998) J. Control Release, 52, 53-62);

Poly(vinyl alcohol) (PVA) hydrogel nanoparticles (Wang et al., (1999) Pharm Res. 16, 1430-1435);

Poly(D,L-lactic acid) nanoparticles (Landry et al., (1996) Biomaterials, 17, 715-723);

Micellar nanoparticles (U.S. Pat. No. 5,629,021) or polymeric micelles or vesicles composed of amphiphilic block copolymers (Rijcken et al., (2007). J. Control Release, 120, 131-148, and on the worldwide web at ncbi.nlm.nih.gov/pubmed/17582642);

Sugar-based nanoparticles, such as Chitosan- or modified chitosan-based micro/nanoparticulate delivery systems (Methods of their preparation, drug loading, release characteristics, and applications are described in Agnihotri et al., (2004). J. Control Release, 100, 5-28);

Oligoscaccharide cyclodextrins and their derivatives (Challa et al., (2005). AAPS Pharm. Sci. Tech. 14, E329-357);

Micelles (Torchilin, (2000). Eur. J. Pharm. Sci. October; 11 Suppl 2:S81-91; Lukyanov and Torchilin, (2004) Adv. Drug Deliv. Rev. 56, 1273-1289) including those prepared from conjugates of water-soluble polymers, such as polyethylene glycol (PEG) or polyvinyl pyrrolidone (PVP), with phospholipids or long-chain fatty acids; and Dendritic peptides, such as PEGylated polyamidoamine dendrimers (Yang and Lopina, (2006) J. Biomed. Mater. Res. 76, 398-407.

Other carriers include those reviewed in Praetorius and Mandal ((2007) Recent Pat. Drug Deliv. Formul. 1, 37-51).

In one embodiment, the carriers are those described in U.S. Pat. Nos. 4,957,735, 7,780,882, and 5,955,343.

In some embodiments, carriers include fast (seconds or minutes) and slow (days) cargo release particles that discharge their payload upon specific interactions with the targeted ligands. Fast release carriers include particles, such as immunoliposomes (i.e. antibody-conjugated liposomes) that are subjected to bilayer destabilization and site-specific release of liposome contents upon specific target recognition (Ho et al., 1986; Ho et al., 1988). Slow cargo release carriers include polymers that allow payload release through desorption off the polymer surface, diffusion through the particle matrix, diffusion through the polymer wall, particle matrix erosion, and a combined erosion/diffusion process (Soppimath et al., (2001), J. Control Release, 70, 1-20. In some embodiments calcein is used as a fluorescent reporter to demonstrate that a protein payload/cargo is specifically delivered to a wound surface by wound-targeting antibodies.

Wound Targeting Moiety

The term "wound targeting moiety" refers to an antibody or other moiety that selectively binds to an exposed protein, peptide motif or epitope, wherein the exposed protein, peptide motif or epitope is exposed upon wounding. In some embodiments, the wound targeting moiety has an affinity for an exposed protein, peptide motif or an epitope of actin.

The term "peptide motif" refers to the portion of the intracellular, extracellular, or extracellular matrix protein that the targeting moiety binds to. In some embodiments, the wound targeting moiety has an affinity for an exposed protein, peptide motif or an epitope of a ribosomal protein. In some embodiments, the wound targeting moiety has an affinity for an intracellular protein. In some embodiments, the wound targeting moiety has an affinity for a peptide motif or epitope within an extracellular protein or an extracellular matrix (ECM) component that becomes exposed upon wounding, for example at the injury site. In some embodiments, the wound targeting moiety is a fluorescently labeled antibody having an affinity for an exposed protein, peptide motif or epitope. wound targeting moiety binds to an intracellular protein.

In one embodiment, the wound targeting moiety does not bind to an extracellular protein or extracellular matrix protein or peptide motif thereof.

In some aspects, the composition, via its wound targeting moiety or moieties, binds to an exposed protein, peptide motif or epitope residing in a tissue selected from the group consisting of epithelial tissue, connective tissue, muscle tissue, and nerve tissue. In some aspects, the connective tissue is selected from the group consisting of bone, cartilage, tendon, and ligaments.

Examples of proteins and peptide motifs include but are not limited to the following:

cryptic tripeptide arginine-glycine-aspartic acid (RGD) epitopes that are not exposed in the native collagen structure but become exposed in response to mechanical trauma or heat that causes collagen denaturation;

HUIV26 epitopes of collagen IV of the extracellular matrix that become exposed upon trauma;

actin, a normally intracellular protein that can become exposed upon wounding.

collagens I and III, which are among the most abundant arterial wall proteins that become exposed upon trauma;

ribosomal proteins, the most abundant class of intracellular proteins that are universally present and become exposed upon cell lysis caused by trauma;

entactins, which are components of the basement membrane that becomes exposed upon injury;

elastin, a component of the vessel walls that is exposed upon injury;

laminin, also a component of the basement membrane that is exposed in wounded tissue; and cytoskeletal proteins such as actin and tubulin.

Vascular targeting moleculars are reviewed in Hajitou, et al. ((2006) Trends Cardiovasc. Med., 16:80-88).

In one embodiment, the wound targeting moiety is an antibody. In one aspect, the antibody is an antibody to actin protein. In another aspect, the actin protein is present in the liver and is exposed upon injury.

In one embodiment, the wound targeting moiety is not an antibody to myosin or histone. In some aspects, the wound targeting moiety is not an antibody to myosin or histone but is an antibody against an epitope present in a wounded liver.

Wound targeting moieties include polyclonal, monoclonal, chimeric and humanized antibodies (or fragment antigen-binding, Fab fragment, regions thereof) against the specific epitope of interest; nucleic acid (DNA or RNA) or peptide aptamers that bind to a wound target molecule; peptides for specific wound target recognition; and small molecules that recognize and bind to specific moieties of the injury-specific wound target epitope.

Methods for use in preparing the wound targeting moiety include standard methods for generating monoclonal and polyclonal antibodies (using animals or cell-based techniques) or antibody-fragments against a specific target. Other methods for specific ligand generation may also include repeated rounds of in vitro selection or SELEX (systematic evolution of ligands by exponential enrichment) to engineer/generate nucleic acid species that bind to specific molecular targets; yeast two-hybrid system for generation of peptide aptamers; phage display technology for identification of peptide ligands; and high throughput screening technology for the identification of small molecule ligands that bind to specific molecular targets.

Examples of methods for the conjugation of ligands to carriers include, for example, chemical modification of the side chains of the amino acids on the polymer (e.g. gelatin) surface for attachment (e.g. cross linking) of the particles to functional ligands for targeted delivery (Balthasar et al., (2005) Biomaterials, 26, 2723-2732). Other methods may also include covalent conjugation of receptor-specific targeting ligands to PEG strands at the surface of the particles (Olivier (2005) NeuroRx., 2, 108-119). Conjugation techniques may include use of biotinylated (Salem et al., (2001) Biomacromolecules, 575-580), amine-reactive (Yamamoto et al., (1999) Colloids Surfaces B: Biointerfaces, 16, 135-146, 1999; Emoto et al., (2000) Colloids Surfaces B: Biointerfaces, 18, 337-346; Yamamoto et al., (2001) J. Control Release. 77, 27-38; Tessmar et al., (2002) Biomacromolecules, 3, 194-200) and thiol-reactive copolymers (Tessmar et al., (2003) Biomaterials, 4475-4486; Olivier et al., (2002) Pharm. Res. 19, 1137-1143) that permit protein chemical conjugation under nondenaturing conditions (Huwyler et al., (1996). Proc. Natl. Acad. Sci. USA 93, 14164-14169; Roberts et al., (2002) Adv. Drug Deliv. Rev. 54, 459-476). For example, biotinylated PEG-PLA nanoparticles may link biotinylated antibodies through an avidin spacer (Gref et al., (2003) Biomaterials, 24, 4529-4537) or avidin-antibody conjugates (Kang et al., (1995). J Drug Target, 3, 159-165).

Active Agent

The compositions as described herein comprise one or more active wound treatment agents. The term "active agent" and "active agents" as used herein are not intended to encompass nucleic acids which require expression before becoming active. Active agents include but are not limited to the following:

hydrostatic/hemostatic monomeric or polymeric agents (including peptides and peptide analogs);

clotting factors, including Factor VIII and Factor IX;

anticoagulants, such as anti-platelet agents;

anti-inflammatory agents;

growth factors, such as vascular growth factor and epidermal growth factor;

immunomodulating agents, such as cytokines (interleukins and interferons);

anticancer compounds, such as antibodies against growth factors (e.g. VEGF);

bone deposition agents;

scar prevention agents;

compounds that inhibit proteins associated with tissue scarring and repair (TNF-$\alpha$); and wound healing promoting agents, such as tissue regenerating factor.

Methods of Administration

The compositions described herein can be used in the field or in a clinical setting to treat open wounds in a subject resulting, for example, from damage or penetration by a foreign object such as debris from an accident, a projectile, a weapon, a surgical instrument, or from a thermal or chemical burn. The wound can be induced deliberately or accidentally. The term "subject" refers to mammals and includes humans and non-human mammals. The compositions can comprise one or more active agents having different therapeutic effects. Compositions each having different agents can also be used in combination. For example, the compositions or combinations thereof can be used to stop or impede hemorrhaging and/or promote healing process. In some embodiments, the compositions are administered prior to or simultaneous with the closure of the wound.

In another application, the compositions are used as a surgical adjuvant following surgeries of various sorts, including for example, repair of broken bones with delivery of bone deposition agents and scar prevention agents, excision of lesions including tumors or encapsulated masses to prevent tumor re-growth or enhance tissue healing, and prevention of fibrosis formation following surgical excision. In another use, the compositions as described herein are used to accelerate wound healing or prevent scarring following plastic surgery.

In general, the compositions containing the active agent will be administered in a therapeutically effective amount. The actual amount administered will depend upon numerous factors such as the nature of the active agent, the severity of the wound, the age and relative health of the subject, and other factors. All of these factors are within the skill of the attending clinician, medical professional or other end user.

The compositions described herein can be in various forms appropriate for the carrier and its active agent and for its administration. Such forms include semisolids, powders, solutions, suspensions, aerosols, or any other appropriate compositions. In one embodiment the composition is administered directly (non-systemically) to the wound site such as by irrigation of the wound with a solution containing a composition described herein. In another embodiment when the wound is an internal wound such as in the case of a bomb blast causing only internal injuries, the composition may be administered systemically such as by intravenous delivery, oral delivery, or by inhalation.

EXAMPLES

The following examples are provided to illustrate certain aspects of the present disclosure. The various working examples presented herein will be used to highlight some features of the present disclosure. However, the present disclosure shall in no way be considered to be limited to the particular embodiments described below.

Example 1

Exposure of a Protein Target in Wounded Tissue

Figure 2:
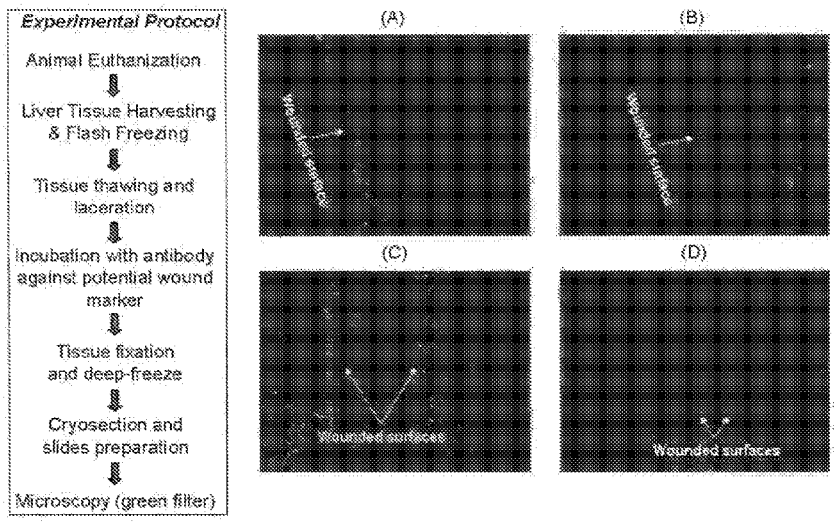
FIG. 2 illustrates specific exposure of a protein target (actin) in wounded rat liver tissue.

Liver from healthy male Sprague-Dawley Rats was harvested and an X-shaped wound was immediately performed on a liver lobe using lab scissors. Cold blocking solution (1 ml of 10% FBS in PBS) was gently pipetted into wound, and whole lobe was placed in 5 ml cold blocking solution in 50 ml conical and incubated for 1 hour @4° C. Antibody solution (500 ul diluted at 1:50 in blocking solution) was then gently pipetted into wound, and lobe was incubated at 4° C. for 1 hour. Antibody, solutions may, for example, include FITC-labeled antibody against the potential injury-specific target epitope and fluorescently labeled anti-Mouse IgG (the latter as a negative control). After antibody incubation, 1 ml cold PBST (0.1% Tween-20 in PBS) was pipetted into wound to wash away unbound antibody. The lobes were then placed in 35 ml cold Neutral Buffered Formalin and incubated at 4° C. overnight to fix the tissue. Liver lobes were then placed in 35 ml cold 30% Sucrose/PBS overnight for cryoprotection. The lobes were then mounted into cryomolds in OCT medium, with X-shaped wound facing the bottom of the cryomold, and placed at −80° C. Cryosections (10 microns thick) are mounted on microscope slides and slides were washed 1× in PBS, mounted with cover slips and viewed using an Inverted Microscope. Images were captured using a digital camera connected to the microscope using appropriate (e.g. Picture Frame) software. A schematic description of the experimental protocol as well as the identification of a wound-specific marker (actin) is illustrated in FIGS. 1 and 2. In FIG. 1, the left panel outlines the experimental procedure. In the right panel: (A) Traumatized tissue incubated with fluorescein-ated ("FITC-labeled") antibody against target protein (10× magnification). (B) Traumatized tissue without antibody (10× magnification). (C) Same as A at 40× magnification. (D) Same as B at 40× magnification. FIG. 2 shows specific exposure of a protein target upon wounding. The left panel outlines the experimental procedure. Right panel: (A) and (C) Traumatized tissue incubated with FITC-labeled antibody against target protein. (B) and (D) Traumatized tissue incubated with non-specific labeled anti-mouse IgG (Negative controls) All pictures were taken at 10× magnification.

Figure 3:
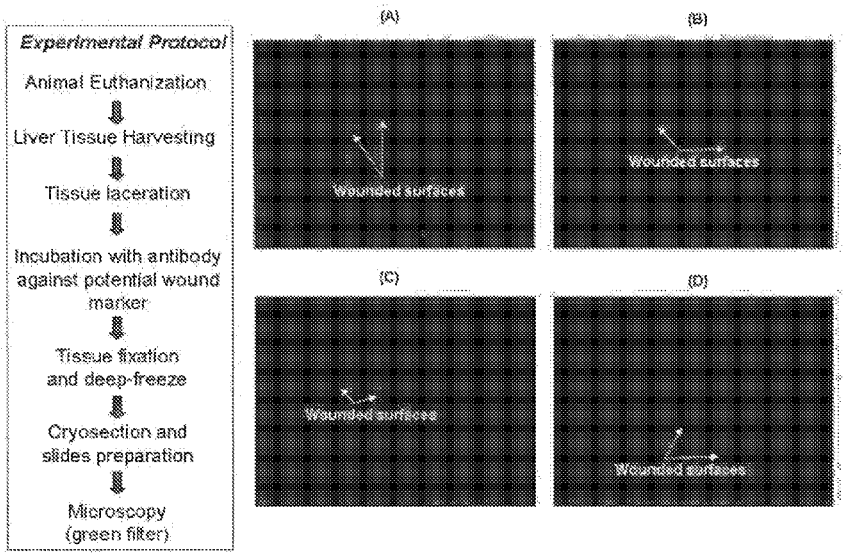
FIG. 3 illustrates specific exposure of actin protein (but not of histone or myosin intracellular proteins) in wounded rat liver tissue.

A comparison of wounded tissue treated with antibodies against actin, histone, and myosin is shown in FIG. 3. The left panel outlines the experimental procedure. Right panel shows wounded tissue incubated with FITC-labeled antibody against the following proteins: actin (A), histone (B), myosin (C). Non-specific labeled anti-mouse IgG was used as negative control (D). All pictures were taken at 10× magnification. Actin antibody was found to bind to wounded surfaces of the tissue, whereas no or negligible binding was seen with the histone and myosin antibodies. These results indicate that not all proteins exposed upon tissue injury are viable targets for delivery of an active agent to a wound site. The results further establish that actin protein is an important target, particularly for the delivery of a composition as described herein to wounded liver tissue.

Example 2

Specific Exposure of an Extracellular Protein Domain (RGD Tripeptide) Target in Wounded Liver.

Figure 4:
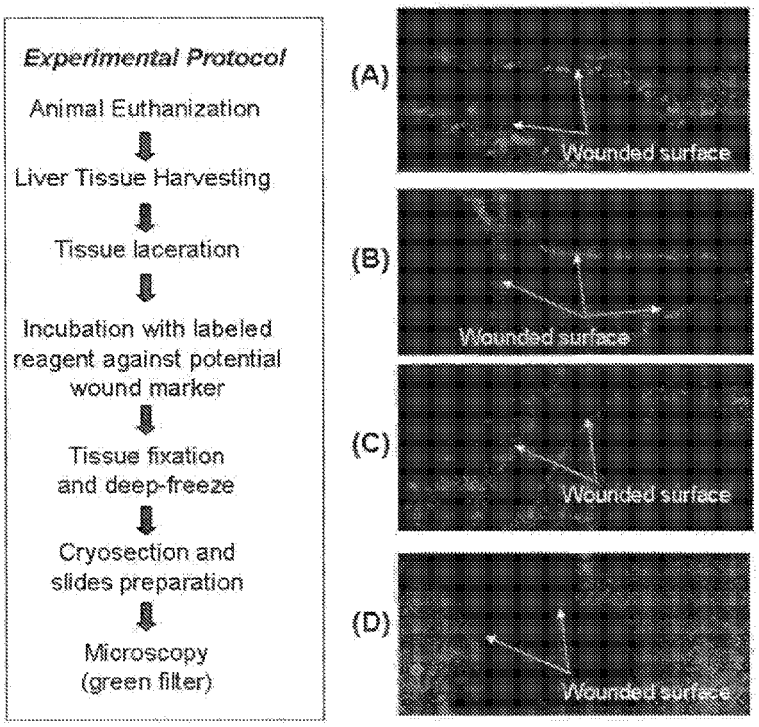
FIG. 4 illustrates specific exposure of an extracellular protein domain target (RGD tripeptide) in wounded rat liver tissue.

Injury of the blood vessel walls and surrounding extracellular matrix by mechanical rupture or heat results in collagen denaturation, a condition where hydrogen bonds that stabilize the triple-helical structure of the collagen molecule break, and the molecule unfolds irreversibly from its native state (Wright and Humphrey, (2002). Annu. Rev. Biomed. Eng. 4, 109-128). Collagen denaturation exposes cryptic tripeptide arginine-glycine-aspartic acid (RGD) epitopes that are not exposed in the native protein structure (Davis, (1992) Biochem. Biophys. Res. Commun. 182, 1025-1031; Pfaff et al., 1993). Upon injury of the extracellular matrix, collagens are the major source of exposed RGD-containing peptides. Although several members of the extracellular matrix proteins family contain RGD sequences, only collagen RGD epitopes are not exposed in the native protein structure (Davis, (1992) Biochem. Biophys. Res. Commun. 182, 1025-1031; Pfaff et al., (1993). Exp. Cell Res. 206, 167-117). The exposed collagen RGD sites facilitate the interaction of damaged extracellular matrix with local arteriolar smooth muscle vβ3 integrins (Davis, (1992) Biochem. Biophys. Res. Commun. 182, 1025-1031), acting as wound recognition signals to cause arteriolar vasodilation and increase in blood flow to the injured area (Mogford et al., (1996) Circ. Res. 79, 821-826). We hypothesized that denatured collagen RGD domains would represent promising targets for wound-specific recognition and delivery of active agents. We tested this hypothesis in animal tissues from euthanized animals using specific RGD recognition peptides that have structures that functionally mimic the RGD-binding site on integrin molecules (e.g. D'Souza et al., (1994) Cell, 79, 659-667). A second specific epitope wound target was found to be the extracellular denatured collagen RGD domains, exposed in injured but not in healthy tissue (FIG. 4). The left panel outlines the experimental procedure. Right panel: injured tissue was incubated with fluoresceinated anti-RGD peptides (panels A, B, C). Non-specific labeled anti-mouse IgG was used as negative control (D). Injury of blood vessel walls and surrounding extracellular matrix results in collagen denaturation, which exposes cryptic tripeptide arginine-glycine-aspartic acid (RGD) epitopes that are not exposed in the native protein structure. Specific recognition of these peptide domains was accomplished using fluoresceinated peptides that have a structure that functionally mimic the RGD-binding site on integrin molecules.

Example 3

Specific Exposure of Actin Protein in Wounded Rat Spleen

Figure 5:
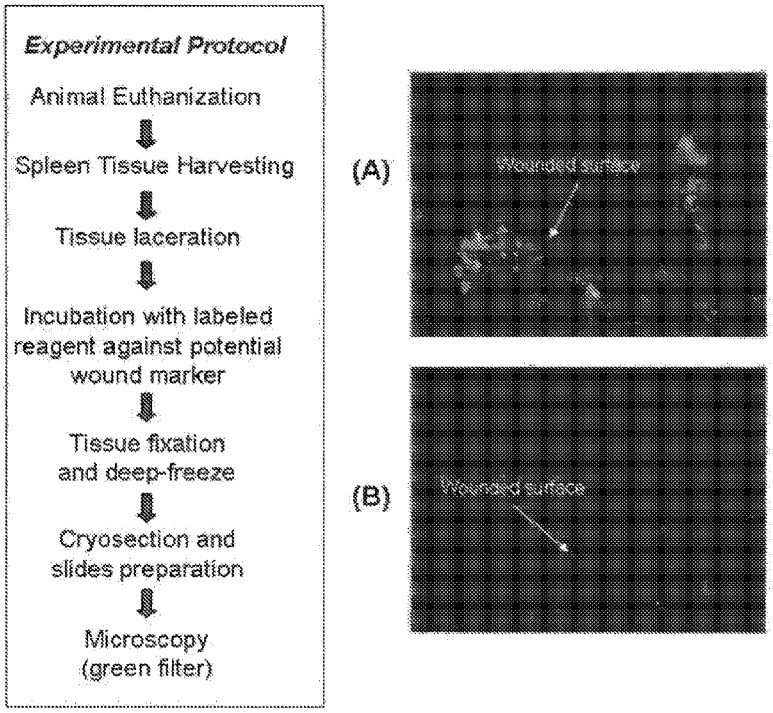
FIG. 5 illustrates specific exposure of actin protein in wounded rat spleen.

Actin was also verified as a wound-specific intracellular target exposed at injured sites in splenic tissue (see FIG. 5). The left panel outlines the experimental procedure. Right panel: wounded tissue was incubated with FITC-labeled antibody against actin (A). Non-specific labeled anti-mouse IgG was used as negative control (B). Thus, actin serves as a wound target for recognition of injured sites on a variety of tissues.

Example 4

Targeting of an Injury-Specific Epitope in the Presence of Blood

In some cases, the liver section was excised at t=0, and the rat was allowed to bleed for 1 minute, blood collected, allowed to bleed for an additional 4 minutes, blood collected, the wound-targeting composition or control applied to the wound over 30 second time period (dropped onto the wound in the presence of residual blood flow), and the sample left to incubate an additional one minute and 30 seconds. The animal was then euthanized, liver harvested, washed, fixed and sectioned.

Figure 6:
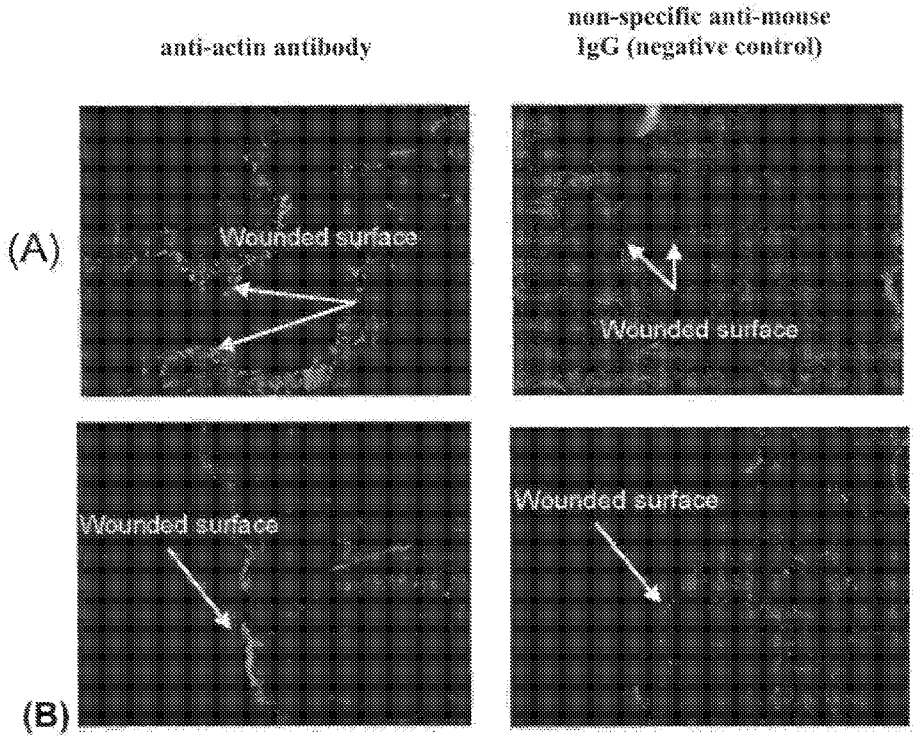
FIG. 6 illustrates wound-specific targeting of an epitope (of actin protein) in the presence of blood in wounded rat liver tissue.

As shown in FIG. 6, excised wounded liver tissue was immersed in blood followed by treatment with FITC-labeled antibody against specific target (anti-actin, left column) or FITC-labeled negative control antibody (IgG, right column). (A) Liver. (B) Spleen. These results indicate injury-specific exposure of the actin epitope in different tissue types and targetability of this epitope in the presence of blood.

Example 5

Time Course Assessment of Wound-Specific Binding

Figure 7:
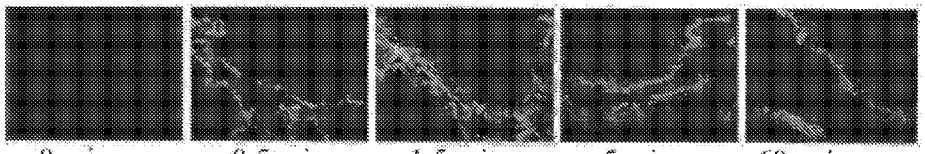
FIG. 7 presents the results of a kinetic evaluation of wound-specific targeting of actin epitopes in injured rat liver tissue.

The kinetics of wound-specific targeting are shown in FIG. 7. Fluorescent images from time course experiment assessing wound-specific binding of fluoresceinated anti-actin antibodies to injured rat liver ex vivo. Time points for incubation include 0 minutes (no antibody), 0.5 minutes, 1.5 minutes, 5 minutes, and 60 minutes. These results suggest that under these experimental conditions, wound-specific binding occurs within 30 seconds.

Example 6

Wound-Specific Exposure of Actin Protein in Wounded Swine Tissue

Figure 8:
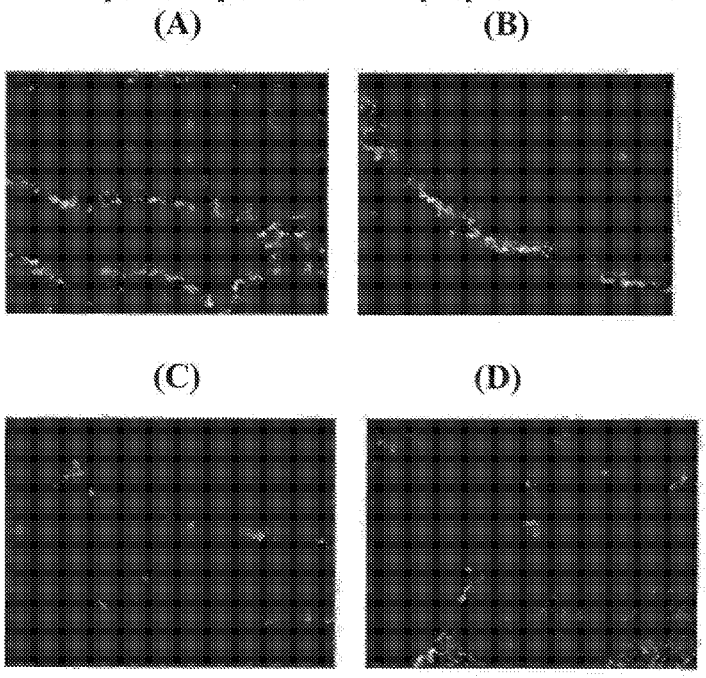
FIG. 8 illustrates wound-specific exposure of actin epitopes in swine liver tissue.

Wound-specific targeting was confirmed in injured tissue from not only small animals (rats) but also large animals (swine). Excised injured swine liver tissue was treated with fluoresceinated anti-actin (A and B) or anti-IgG (negative control) (C and D). (FIG. 8). Wound-specific exposure of actin epitopes was observed in swine tissue. These results confirm wound targeting in injured tissue from large animals.

Example 7

Anti-Actin-Conjugated Beads also Specifically Bind Wounded Liver Tissue

Figure 9:
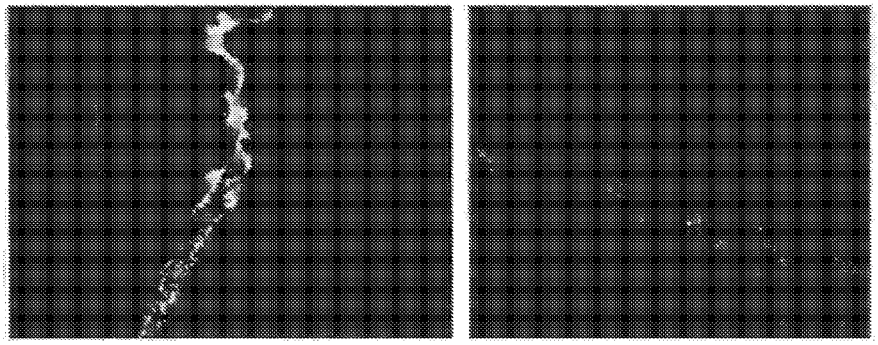
FIG. 9 shows fluorescence of beads conjugated to anti-actin in wounded liver tissue ex vivo.

FIG. 9 shows that beads conjugated to anti-actin antibody molecules recognize wounded liver tissue. Frozen liver was thawed, wounded, and incubated with labeled polystyrene beads conjugated to either anti-actin or anti-human IgM (negative control). The wound was washed four times, and the liver tissue was then fixed, cryprotected, mounted and frozen followed by cryosection. (A): Beads tagged with anti-actin antibodies. (B): Beads tagged with IgM (Negative Control).

Example 8

Validation of Wound-Specific Markers in vivo

Figure 10:
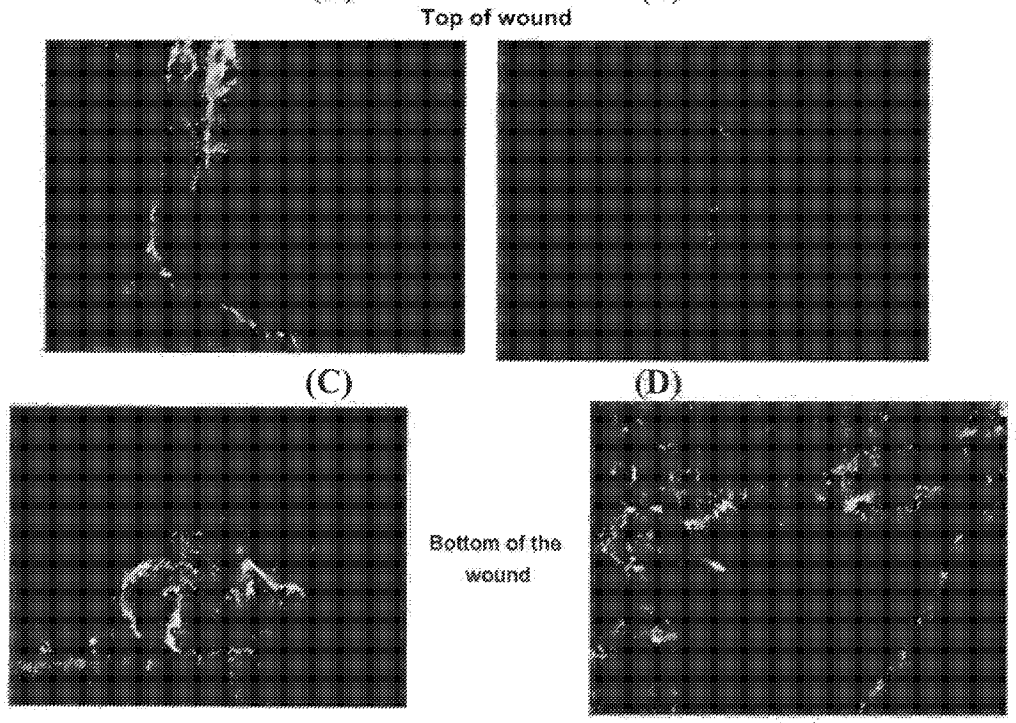
FIG. 10 shows validation of wound-specific markers (actin) in wounded liver tissue in vivo.

Transport and wound-specific binding was tested in vivo using surrogate cargo carriers (polystyrene beads) conjugated to antibodies recognizing actin epitopes exposed at the wounded area in an aggressively bleeding liver model in rats. Rats were anesthetized with isoflurane and subjected to mid-line ventral incision. The large liver lobe was isolated and wounded through excision of a section of the ventral surface of the large liver lobe with a curved set of surgical scissors, generating a grade V open abdomen trauma. Exemplary wounds were approximately 1-1.5 cm×0.75 cm×0.4 cm (2.1-5.6% of the total liver weight, as determined post-experimentation; approximate "divot" volume=600-700 μL. Wounded animals were treated with fluorescently labeled polystyrene beads (2 microns in diameter) in the presence of blood flow. Polystyrene beads were tagged with either anti-actin antibodies (for wound targeting) or anti-IgG (negative control). Following treatment, the animals were euthanized, the livers were harvested, washed, fixed and sectioned for fluorescent microscopy. FIG. 10 shows fluorescent images of tissue sections from the top of the wound. (A): Beads tagged with antibodies against actin. (B): negative control beads. Tissue sections from the bottom of the wound were also sectioned and stained, and are shown in (C) and (D). The results provide evidence for wound-specific exposure of actin epitopes in vivo and proof of feasibility for use of this target for specific delivery of agents to a bleeding site.

Example 9

Evaluation of Ribosomal Proteins as Wound-Specific Targets

Figure 11:
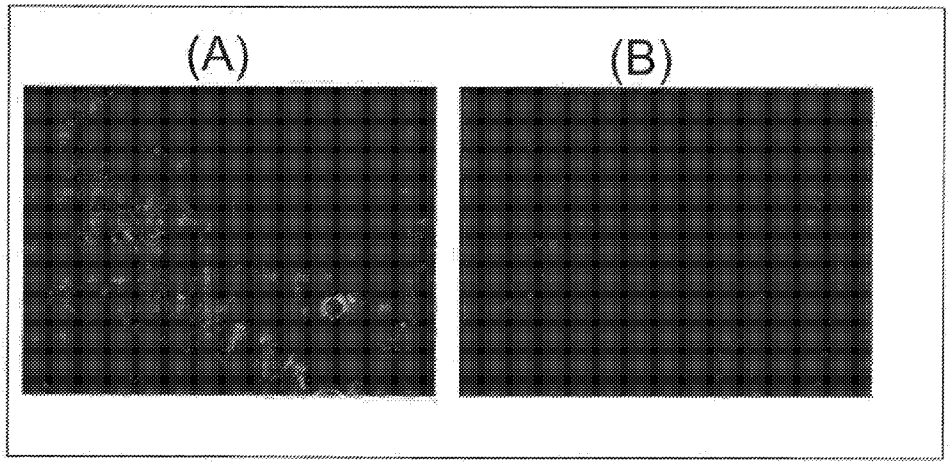
FIG. 11 illustrates results of evaluation of wound-specific exposure of ribosomal protein S6 in wounded liver tissue ex vivo.

Ribosomal proteins are the most abundant class of intracellular proteins, present in all organisms. Ribosomal protein S6 was hypothesized to be a wound-specific target, and experiments were performed to assess its wound-specific exposure in rat tissue ex vivo. Excised injured rat liver tissue treated with fluoresceinated anti-rpS6 (A) or anti-IgG (negative control) (B). (FIG. 11). No significant exposure of rpS6 epitopes in injured areas was observed following bleeding and immunohistochemistry.

Example 10

Hemostatic Activity of Peptide Agent in Animal Model of Injury

Identification of injury-exposed epitopes would enable the targeted delivery of active wound treatment products, including but not limited to hemostatic agents. One category of hemostatic agents comprises peptides that self-assemble into β-sheet nanofibres forming a stable hydrogel scaffold when exposed to physiological salt conditions (Yokoi et al., (2005). Proc. Natl. Acad. Sci. USA. 102, 8414-8419). These peptides have been successfully used to rapidly stop bleeding when applied locally to a wound in the brain, spinal cord, femoral artery, liver, or skin of mammals without the use of pressure (Ellis-Behnke et al., (2006). Nanomedicine, 2, 207-215). Our studies have developed lead peptides that a) are soluble and easy to handle, b) self-assemble under physiological Na+ conditions similar to those present in the wound environment, c) have rapid self-assembly kinetics within time limit criteria for achieving hemostasis, and d) create hydrogels with a stiffness demonstrated to produce hemostasis in literature reports of other hydrogel-forming peptides.

Figure 12:
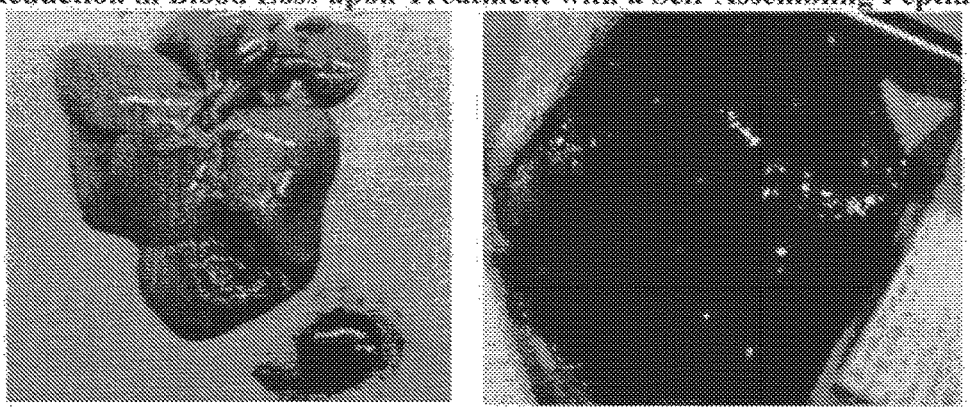
FIG. 12 show that a self-assembling peptide, AMAX3WW, forms a hydrogel when delivered to rat liver in vivo and exhibits hemostatic activity at the wound site.
Figure 12:
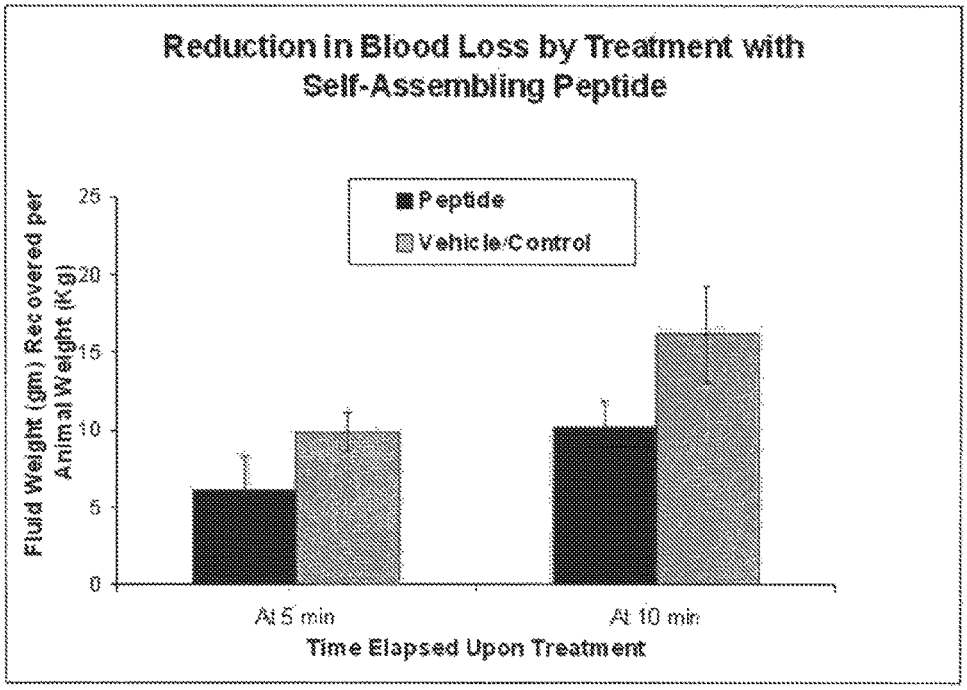

The self-assembling peptide AMAX3WW demonstrated hemostatic activity in an animal model of arterial bleeding. Rats were anesthetized with isoflurane and subjected to mid-line ventral incision. The large liver lobe was isolated and wounded through excision of a section of the ventral surface of the large liver lobe, generating a grade V open abdomen trauma. Relative to vehicle control, treatment with a self-assembling peptide AMAX3-WW significantly reduced fluid loss (~40%) at 5 and 10 minutes post treatment and restored near normal blood pressure. In contrast, control-treated animals went into respiratory arrest due to continued bleeding and dilution of blood by infused fluids. FIG. 12: Top left panel: typical liver injury generated by excision of a section of the ventral surface of the large liver lobe. Top right panel: hydrogel formation on liver in vivo upon administration of 3 mL of 4% AMAX3-WW peptide. Bottom panel: Effect on bleeding at 5 and 10 minutes post-treatment with hemostatic peptide or control vehicle. Blood loss estimation was based on weight of gauze sponges collected from wounded area.

Example 11

Liposomes Carry Protein Payload to Wounded Tissue

Figure 13:
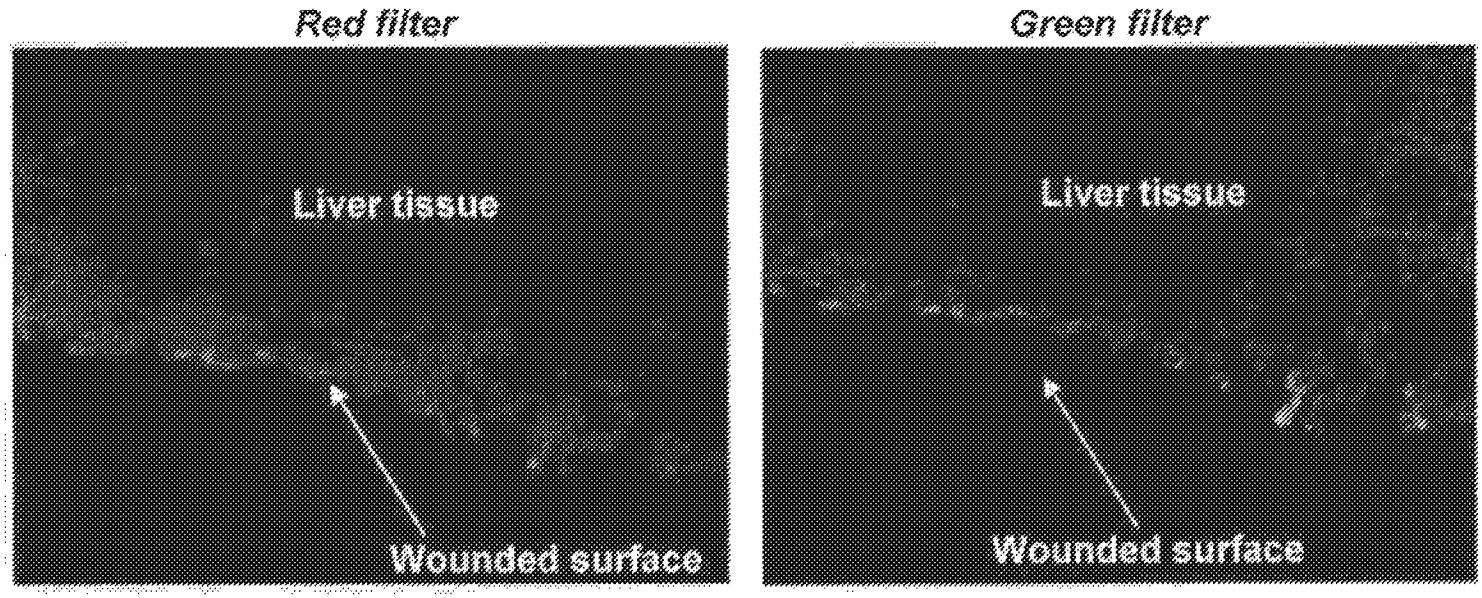
FIG. 13 shows co-localization of protein cargo (calcein)-carrying liposomes conjugated to wound-targeting antibodies and specific delivery at the wounded surface.

Calcein was used as a fluorescent reporter to demonstrate that a protein payload/cargo was specifically delivered to a wound surface by wound-targeting antibodies. Wounded tissue was stained with Rhodamine (red)-labeled liposomes carrying a green-labeled cargo (calcein) protein. FIG. 13 shows co-localization at the wounded surface of liver tissue of the calcein payload and the liposomes conjugated to wound-targeting antibodies.

The present disclosure refers to the following references below. All references, patent applications, and patents identified herein are incorporated by reference into this application in their entirety.

What is claimed is:

1. A method for treatment of an open wound in a subject, comprising administering to the open wound a composition comprising a carrier containing a hemostatic *active* agent, and a wound targeting moiety comprising an antibody specific for actin, wherein the carrier is conjugated to the antibody, and wherein the antibody facilitates local delivery of the hemostatic active agent to wound tissue by binding to an exposed actin protein, wherein the exposed actin protein is exposed upon wounding of the subject.

2. The method of claim 1, wherein the antibody binds to an exposed intracellular actin protein.

3. A method for treatment of an internal wound in a subject, comprising administering to the subject a composition comprising a carrier containing a hemostatic active agent and displaying a wound targeting moiety comprising an antibody specific for actin, wherein the antibody facilitates local delivery of the hemostatic active agent to injured tissue by binding to an intracellular actin protein that is exposed by displacement from its natural location.

4. The method of claim 3, wherein the intracellular actin protein is exposed by cell lysis or rupture.

*5. The method of claim 1, wherein the administering is performed by irrigating the wound with the composition.*

*6. The method of claim 3, wherein the administering is performed by intravenous delivery of the composition.*

*7. The method of claim 3, wherein the administering is performed by oral delivery of the composition.*

*8. The method of claim 3, wherein the administering is performed by inhalation of the composition.*

* * * * *